United States Patent [19]
Guirguis

[11] Patent Number: 5,016,644
[45] Date of Patent: May 21, 1991

[54] URINE TESTING MODULE AND METHOD OF COLLECTING URINE ANTIGEN

[75] Inventor: Raouf A. Guirguis, Rockville, Md.

[73] Assignee: La Mina Ltd., British Virgin Isls.

[21] Appl. No.: 412,019

[22] Filed: Sep. 25, 1989

Related U.S. Application Data

[63] Continuation-in-part of Ser. No. 408,547, Sep. 18, 1989, which is a continuation-in-part of Ser. No. 308,763, Jan. 10, 1989, Pat. No. 4,961,432, and a continuation-in-part of Ser. No. 396,655, Aug. 22, 1989, which is a continuation-in-part of Ser. No. 369,610, Jun. 21, 1989.

[51] Int. Cl.$^5$ .............................................. A61B 5/00
[52] U.S. Cl. ...................................... 128/771; 604/317
[58] Field of Search ................. 128/760, 761, 771; 604/317, 318, 403, 404; 422/102

[56] References Cited

U.S. PATENT DOCUMENTS

| | | | |
|---|---|---|---|
| 3,312,221 | 4/1967 | Overment | 604/317 |
| 4,473,530 | 9/1984 | Vilk-Real | 128/762 |
| 4,492,258 | 1/1985 | Lichtenstein et al. | 128/761 |
| 4,661,100 | 4/1987 | Rechsteiner | 604/317 |
| 4,685,472 | 8/1987 | Muto | 128/760 |

FOREIGN PATENT DOCUMENTS

PCT/US89/-02914  6/1989  PCT Int'l Appl.

Primary Examiner—Max Hindenburg
Attorney, Agent, or Firm—Gipple & Hale

[57] ABSTRACT

A method for testing for biological molecular indicators in urine. Urine is transported through a sample container under pressure to flow through the sample container so that antigens in the urine are collected and bound on antibodies immobilized on the beads to form antigen-antibody complex. The beads are washed to remove cell debris and charged molecules and a specific prelabelled antibody solution is passed through the sample container with the prelabelled antibodies attaching to a receptor site on the captured antigen to form an antibody-antigen-prelabelled antibody sandwich complex. This sandwich complex is washed to remove cell debris and charged molecules and mixed with a color reagent solution which reacts with the prelabelled antibody to produce an color indicating the presence of a specific cancer antigen.

14 Claims, 4 Drawing Sheets

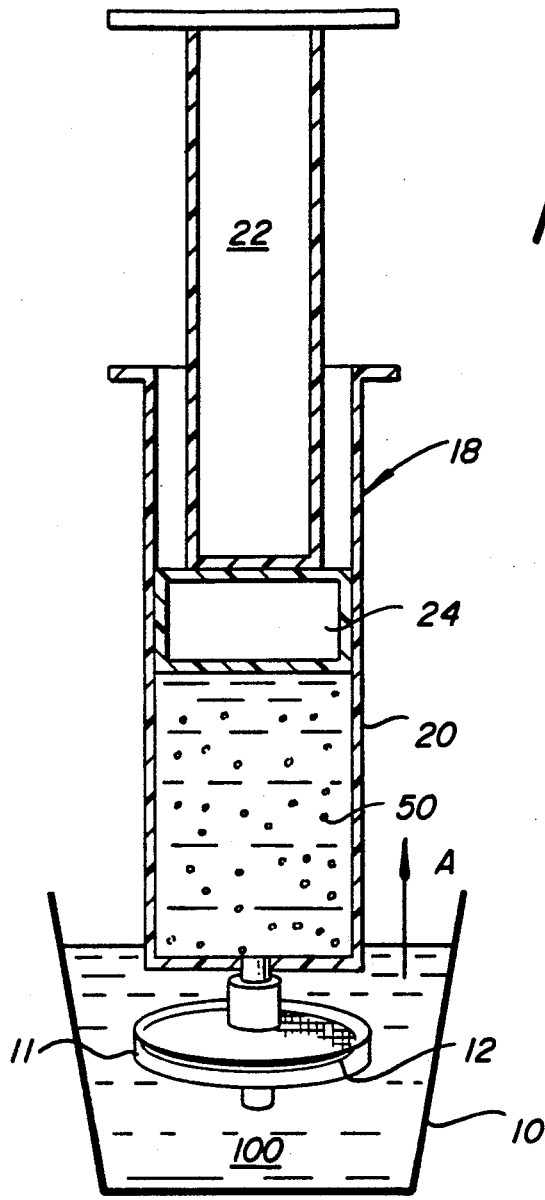
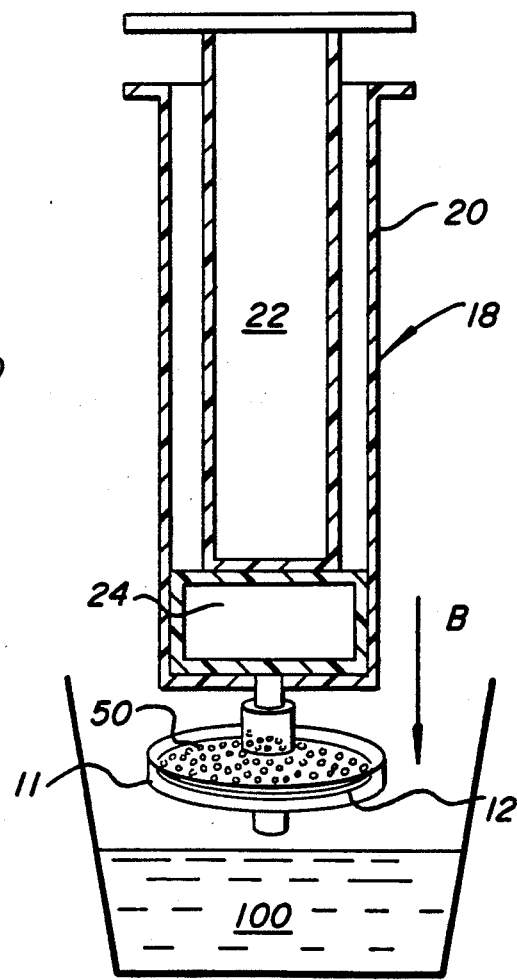
FIG. 2
FIG. 3

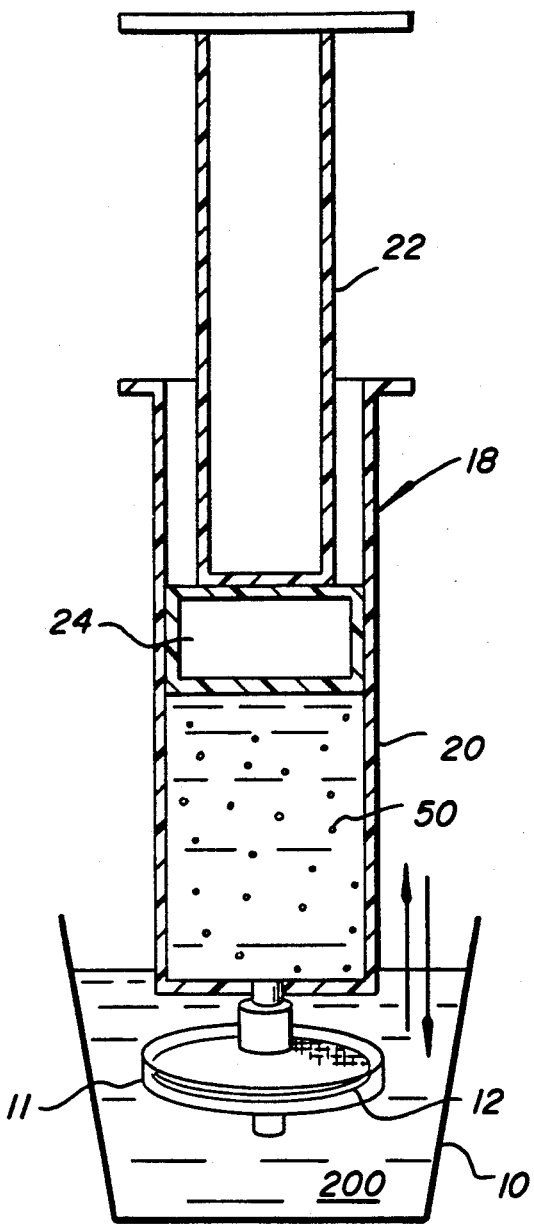
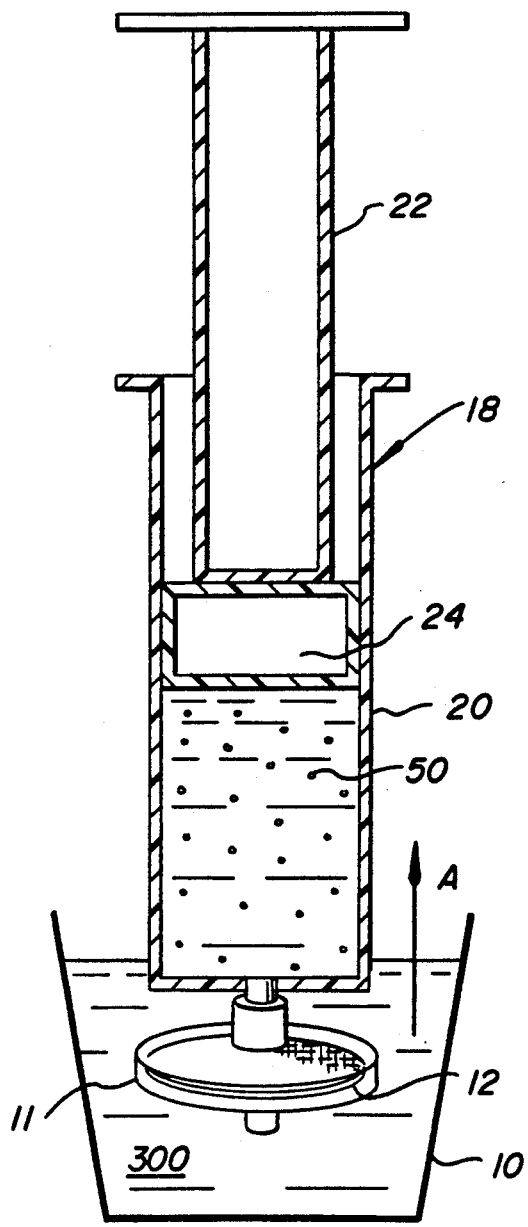
FIG. 4
FIG. 5

URINE TESTING MODULE AND METHOD OF COLLECTING URINE ANTIGEN

RELATED CASES

This application is a continuation-in-part application of U.S. patent application Ser. No. 07/408,547 filed Sept. 18, 1989 pending which is a continuation-in-part of U.S. patent application 07/308,763 filed Jan. 10, 1989 U.S. Pat. No. 4,961,432 and U.S. patent application Ser. No. 396,655 filed Aug. 22, 1989 pending which is a continuation-in-part of U.S. patent application Ser. No. 07/369,610 filed June 21, 1989, pending.

BACKGROUND OF THE INVENTION

The present invention is directed to medical and laboratory fluid specimen collecting and testing apparatus, and more specifically to an apparatus for testing for the presence of specific antigens in biological fluids.

The family of immunoassay works upon the simple principle that is the specific recognition of an antigen by an antibody. Thus specific antigen detection and quantification requires an antibody which recognizes the uniqueness of an antigen. The antigen binding site of antibodies recognizes about six amino acids or their equivalent in mass. One unique binding site serves as an identifying marker for that protein.

When a definitive antibody for a given antigen is available it is used to identify the antigen in the sample mixture. Once the antibody combines with the antigen a means is needed to recognize the complex. There presently exists a need to concentrate antigens from volumes of fluid when the antigen is not present in measurable quantities in specific fluid volumes.

The present invention is directed toward a method which can use immunoassay in sample treatment apparatus for diagnostic and testing purposes of specific urine antigen by concentrating the specific urine antigen by capturing it with an immobilized antibody on a bead in a small volume area, washing the antigen-antibody complex, engaging the antigen-antibody complex with a solution of prelabelled primary antibody so that the captured antigen bonds with the prelabelled primary antibody as a sandwich complex and mixing the antigen-antibody sandwich complex with a coloring reagent to obtain a test color.

It is generally necessary in diagnosing and testing for many diseases to collect biological fluids from a patient, e.g., sputum, blood, pleural and peritoneal cavity fluids, urine, etc. for analysis. It is important during the collection handling of biological fluid specimens that the potential of specimen contamination and the spread of any infection from the specimen be minimized. While urine is commonly collected in 100 ml containers the actual urine testing is commonly conducted with relatively small amounts of sample around 0.2-0.5 ml in volume. Thus because of the small test quantity, cancer producing antigen can only be ascertained after the cancer is in an advanced or late tumor stage. The rest of the urine sample is used for further testing or is thrown away. Additional problems occur in shipment when dealing with urine because of the relatively large volume of fluid involved in the collection specimen sample. There is also the risk of sample deterioration because of the relatively short sample shelf life of urine unless kept in specific temperature conditions. In addition there is also the potential for specimen damage or spillage during the collection and/or shipment process as well as the potential for destruction of certain molecular components of the specimen such as antigens contained therein, because the packaging does not protect the urine or causes chemical changes of different fluid components which will negate the test results or result in false data being obtained when the specimen is tested.

There currently exists a need to provide a test procedure to test for molecular components of biological fluids for the presence of cancer at an early stage in the development of the cancer.

A typical specimen collecting apparatus is shown by U.S. Pat. No. 4,741,346. This apparatus includes a base stand which supports the specimen vial in an upright position. A funnel is inserted in the open end of the specimen vial and surrounds and encloses the upper portion of the vial. The base stand has an upwardly extending tubular wall which at least partially surrounds the vial in connection with the cap and allows the user to remove the vial without touching the surface or coming in contact with the specimen. Examples of various types of liquid containers for collecting and transporting urine are shown by U.S. Pat. Nos. 3,777,739; 3,881,465; 4,042,337; 4,084,937; 4,244,920; 4,492,258 and 4,700,714.

Another specimen collection device shown by U.S. Pat. No. 4,040,791 discloses a collection receptacle having a nipple upon which is mounted a specimen container which receives a predetermined amount of the specimen in a sealed condition. The specimen container is provided with an integally formed cap which is placed over the opening in which the collector nipple is inserted. U.S. Pat. No. 4,557,274 discloses a midstream urine collector having a funnel which transmits urine into a cup member which is covered by a membrane cover.

A combined strip testing device and collection apparatus is shown by U.S. Pat. No. 4,473,530 and is directed to an apparatus which integrates testing and collection by having chemical reagent test strips present within the tube together with specific gravity reading means allowing immediate testing of the urine. U.S. Pat. No. 4,573,983 is directed towards a liquid collection system having an antiseptic member on the discharge section which uses a filter of air and bacteria impervious material to filter the urine.

It is therefore desirable to provide an easy to handle method for allowing more sensitive cancer detection from the sample while also providing that the test specimen can be compactly stored for a period of time in concentrated form allowing cancer testing to be performed quickly and accurately by distal testing facilities with minimum elapse of time.

BRIEF SUMMARY OF THE INVENTION

The invention is directed toward a urine antigen testing process. This method uses a removable stackable sealed urine antigen sample container having an interior chamber with primary antibody covalently bound to beads. The urine is pumped through the container where it engages and passes through a filter which allows passage of filtered urine fluid and antigen through an antibody bead bed. The beads in the bead bed have specific antibodies covalently bound thereto to capture specific antigen carried by the urine fluid. The resultant antigen-antibody complex and associated beads are washed and then recombined with prelabelled primary antibodies in solution to form a sandwich complex. The sandwich complex is washed and combined with coloring reagents to give a color indication if a cancer marking antigen is present in the urine.

It is thus an object of the invention, particularly where ligands such as antigens ar being removed from the body fluids for testing to provide a easy visual color test to determine the presence of specific antigens in the body fluid samples. Previously such testing has been accomplished by a series of tests involving a number of different containers and expensive laboratory equipment of a limited sensitivity.

In the accompanying drawings, there is shown an illustrative embodiment of the invention from which these and other of objectives, novel features and advantages will be readily apparent.

BRIEF DESCRIPTION OF THE DRAWINGS

FIG. 2 is a cross sectional schematic view of the device of FIG. 1 showing the urine test container immersed in urine with urine entering the syringe in the direction of movement shown by arrow A for antigen capture;

FIG. 3 is a cross sectional schematic view of the device of FIG. 1 showing sequential movement of the syringe plunger from that shown in FIG. 2 with urine being discharged from the syringe with direction of movement shown by arrow B and the immobilized antibody beads and captured antigen positioned in the test container;

FIG. 4 is cross sectional schematic view of the syringe plunger shown in FIG. 3 after the urine has been fully discharged from the syringe, washing the beads to separate cells, unbound ligands and debris from the antigen-antibody on the beads;

FIG. 5 is cross sectional schematic view of the container after washing as shown in FIG. 4 mixing the antigen-antibody complex with prelabelled primary antibody solution to obtain a sandwich complex bead;

DETAILED DESCRIPTION OF THE INVENTION

Figure 1:
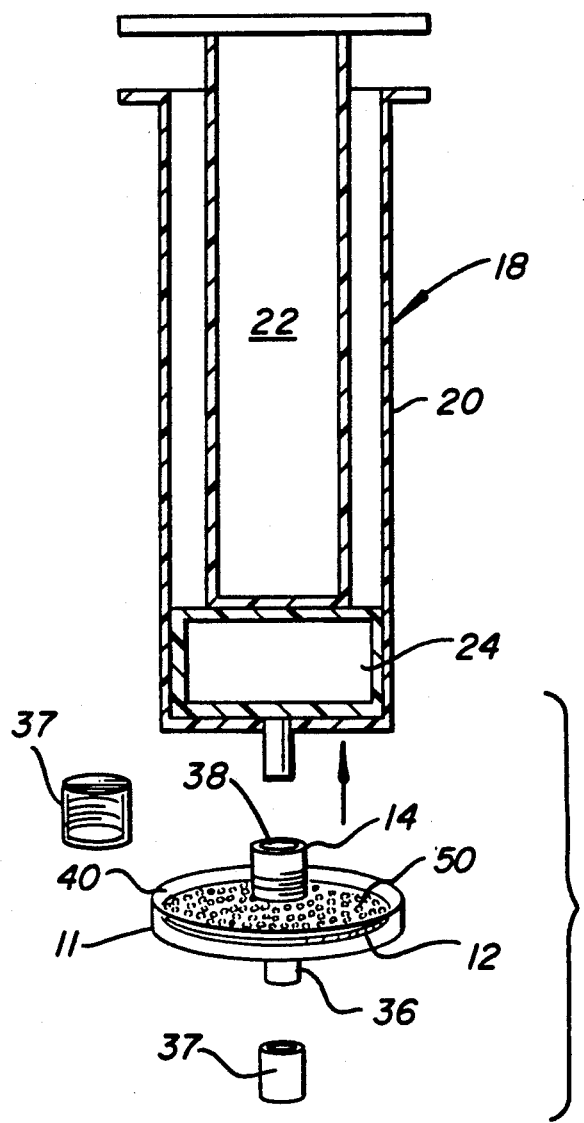
FIG. 1 is an exploded cross sectional schematic view of the inventive urine testing device.
Figure 6:
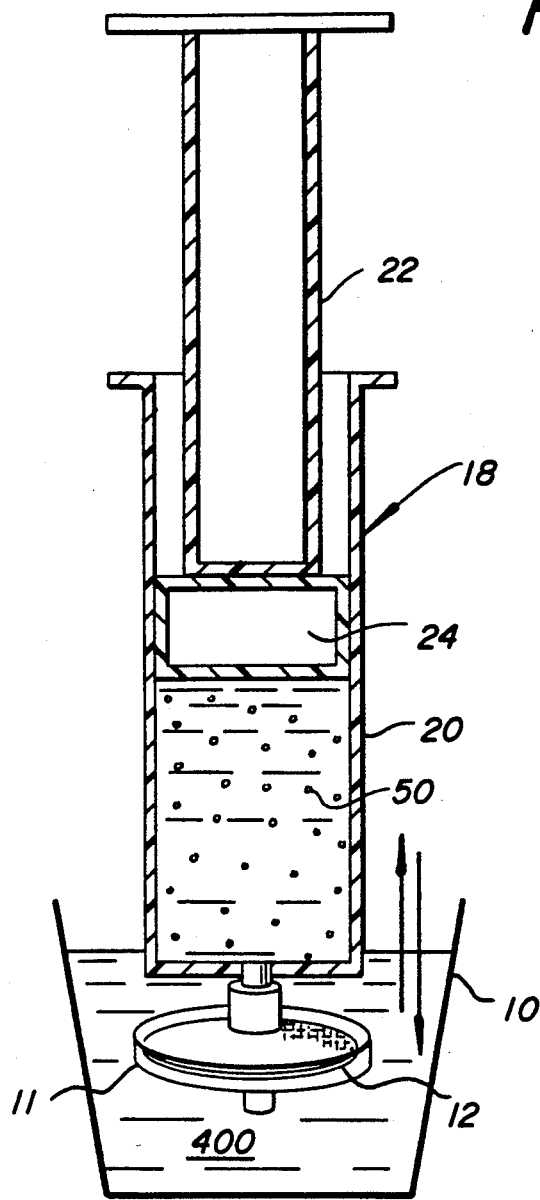
FIG. 6 is cross sectional schematic view showing mixing of the sandwich complex beads after washing as shown in FIG. 4 with coloring reagents which react to the prelabelled primary antibody on the sandwich complex to present a readable test color.
Figure 7A:
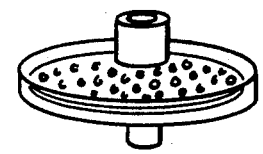
FIGS. 7(a)–(d) are a perspective schematic showing the final results of the test which can be read by the naked eye or using a reader.
Figure 7B:
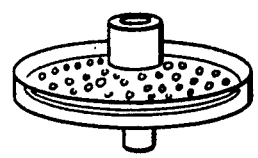
Figure 7D:
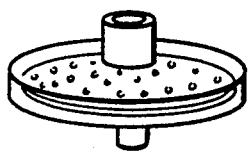
Figure 7C:
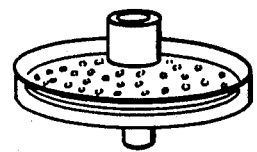

The preferred embodiment and best mode of the invention is seen in FIGS. 1 through 6. The initial collection of the urine is normally housed in a graduated 100 ml container 10. Such a container is currently manufactured by Becton Dickerson Labware under the designation 4013 specimen container. This collection container holds 4.5 oz. (approx. 133 ml) and is graduated with a polyethylene snap lid. The invention utilizes a urine sample container 11 with treatment filter 12 mounted therein. The filter 12 preferably has a filter particle size of 5 microns but can range from 1–5 microns or any size which is suitable to allow fluid flow with antigens to pass therethrough but also prevent the passage of beads 50. The urine sample container 11 can be a disposable sterile single use filter assembly manufactured by Gelman Sciences under the trademark ACRODISC with a 5 VM filter. However, any suitable filter can be used such as the aqueous glass microfiber filter manufactured by Xydex, a subsidiary of Genex Corporation or a membrane member manufactured by Millipore Corporation. One end 14 of the container is fitted with a threaded projection which is adapted to fit onto the luer lock of a 30 cc syringe 18, manufactured by Becton Dickinson & Co. It should be noted that any pump type device could be used in place of the syringe as for example an autovial spunglass filter manufactured by Genex Corporation. The syringe 18 has a barrel 20, piston 22 and piston head 24. While the invention can be used for any body fluid it is primarily designed for use in collecting concentrated urine antigen samples for use in testing for the presence of various kinds of cancer in the body to determine the presence and stage of the cancer.

As shown in FIGS. 1 through 7 a urine sample container 11 is constructed of polystyrene. The container housing has walls which define an urine entrance port 36 and exit port 38. The chamber 40 of the urine sample container contains a filter 12 with a filter size ranging from 0.5 to 5 microns mounted at one end and a bed of beads 50 with immobilized antibodies positioned on the syringe side of the filter.

The beads 50 may be visible so that their flow into the syringe and back to the container can be visually observed to make sure of maximum bead contact with the urine. Antibodies are immobilized (covalently bound) on beads 50 and are designed to have binding sites which have a high affinity for the epitopes of the cancer marking antigens carried in the urine. It should be noted that the volume of beads 50 is important and the beads should not be greater then volume of the container chamber 40 so that the syringe neck will not become jammed.

The principle of affinity chromatography requires that a successful separation of a biospecific ligand is available and that it can be chemically immobilized to a chromatographic bed material, the matrix. Numbers of methods well known in the art have been used to couple or immobilize antibodies to a variety of activated resins. Examples of immobilization techniques which exhibit variable linkage are those formed by the reaction of the reactive groups on the support with amino, thiol, hydroxyl, and carboxyl groups on the protein ligand. The selection of the ligand is influenced by two factors. First, the ligand should exhibit specific and reversible binding affinity for the substance to be purified and secondly it should have chemically modifiable groups which allow it to be attached to the matrix without destroying its binding activity. (Examples of such are Protein G Sepharose manufactured by Pharmacia, Hydrazide AvidGel Ax manufactured by BioProbe International, and Actigel-ALD manufactured by Sterogene Bioseparation Inc.).

An advantage to the use of Actigel-ALD is that it does not cross link proteins therefore allowing proteins to retain high bioactivity after their immobilization. Actigel-ALO SUPER FLOW also available from Sterogene Bioseparation Inc. permits a linear flow rate of up to 3000 cm/h which would fit nicely with the flow rates in the apparatus (approx 10–100 cm/min).

The resin beads 50 with matrix and primary ligand (in this case immobilized antibody) having had flow contact with the filtered urine in buffered form from the addition of 200 ml of M Tris buffer, pH 7.8 manufactured by Pharmacia, captures through antigen-antibody reaction or immune reaction the specific ligand component carried by the urine namely, the non complexed antigen.

The buffer solution can be added to the collection container 10 by directly adding it from the syringe 18 prior to withdrawing the urine into the syringe or simply adding it from another container. When the specific antigen is present in the urine testing sample 100 the antigen reacts with the antibody to form antigen-antibody complexes. The complexed antigen-antibody carried by beads 50 remains in the housing chamber 40. If there is an absence of the antigen in the specimen sample 100 the antibody will remain unoccupied.

As shown by FIGS. 1-3 the container 11 is placed on the luer lock of syringe 18 with ports 36 and 38 opened by the removal of caps 37. The container 11 is screwed into a 30 cc syringe and immersed in urine 100 contained in cup 10. The syringe plunger is pulled withdrawing 25 cc of the urine sample through the container. The syringe is emptied through the container and the steps of withdraw and discharge are repeated until a total volume of 100 cc of the urine sample has come in contact with the antibody beads 50. The antibody beads are carried by the urine into the barrel of the syringe each time the urine is withdrawn from cup 10.

After the urine sample has been processed as described to concentrate the antigen on the antibody beads, the beads are washed by withdrawing 25 cc of washing solution 200 through the container 11 and withdrawing and discharging the syringe three times. This washing carries off cells, debris, and non bonded ligands which may have been attached to the bead matrix or antigen-antibody complex by lodging or charge attraction.

After washing, a solution 300 of 10 ml of prelabelled primary antibody of a 1:500 dilution is prepared. The total amount or 10 ml of the antibody solution 300 is withdrawn and passed through the container 11 to discharge and empty the syringe three times. When the primary labelled antibody solution has been processed so that the primary labelled antibody is bound to the antigen of the antigen-antibody complex to form a sandwich complex, the container is washed as previously described. The container 11 is placed in a coloring solution reagent 400 and 5 cc of coloring reagent is withdrawn into the syringe. The syringe is emptied and the color read in the container.

The color solution or reactant 400 is preferably a substrate manufactured by Kirkegaard & Perry Labs under one of several acronyms namely: ABTS (2,2'-azino-di-[3-ethylbenzthiazoline sulfonate (6)]; OPD (ortho-phenylene diamine); or TMB (tetramethylkbenzidine). In choosing the substrate, the sensitivity of the immunoassay is determined by the discrimination of the antibody reagents. When this occurs, the use of a more sensitive substrate serves only to proportionately increase the signal and the background. The result is more color but the same signal-to-noise ratio. Should the more sensitive substrate push the absorbance over the cut-off of the reader, the faster substrate may in fact reduce the signal-to-noise ratio.

The preferred color solution as used in the embodiment of the present invention is ABTS. The preferred ABTS substrate is a one-component substrate. The HRP label on the primary labelled antibody added after the initial antigen-antibody complex turns ABTS to a blue-green color and there is no change in color or absorbance when the reaction is stopped with SDS (sodium dodecyl sulfate). If the assay optimization indicates the sensitivity of the immunoassay is limited by the color generated by the HRP (horseradish peroxidase) then the more sensitive TMB substrate would give more color development without a corresponding increase in the background. Another advantage of the TMB substrate is that it often lowers the amount of antibody and antigen reagents required for the immunoassay. TMB substrate is a two component liquid substrate and requires hydrogen peroxide. Thus when using this substiate the additional step of immersing in hydrogen peroxide would be required. HRP converts TMB to a blue product. When the reaction is stopped by acidification, the TMB product becomes yellow. ODP is generally provided as a tablet that is dissolved in buffer at the time of use. HRP converts OPD to a yellow product which continues to oxidize into a brown precipitate. Upon acidification the OPD product becomes orange.

As can be seen this antigen-antibody sandwich complex method allows for the first time for the detection of the early stages of cancer as compared with present day testing which can only identify the later tumor stage. Thus the physician now has available the capability of quick testing for cancer patients after surgery or for the testing of patients with suspected cancer.

In the foregoing description, the invention has been described with reference to a particular preferred embodiment, although it is to be understood that specific details shown are merely illustrative, and the invention may be carried out in other ways without departing from the true spirit and scope of the following claims:

What is claimed is:

1. A method of testing for the presence of cancer antigen comprising the steps of:
   a. collecting urine into an apparatus for collecting biological fluids;
   b. passing the urine through a urine treatment container holding an immobilized antibody bead means to capture antigen from the urine;
   c. washing the bead means antibody-antigen complex formed in step b to remove non bound materials,
   d. mixing the bead means antibody complex with a prelabelled primary antibody solution to form a sandwich complex of antibody antigen prelabelled primary antibody;
   e. washing the sandwich complex bead means to remove non bound materials; and
   f. immersing the washed sandwich bead means in a coloring reagent which reacts with the prelabelled primary antibody to produce a color which indicates cancer presence.

2. A method as claimed in claim 1 including repeating steps b and d a plurality of times.

3. A method of testing for predetermined antigen in urine comprising the steps of:
   a. placing an antigen collecting apparatus in fluid communication with urine and causing the urine to pass through the antigen collecting apparatus so that antigens are captured by antibody bead means located in said collecting apparatus forming an antigen-antibody complex bead means;
   b. washing the antigen-antibody complex bead means to remove non bound debris,
   c. causing a prelabelled primary antibody solution to contact the antigen-antibody complex bead means to form an antigen-antibody sandwich complex with the prelabelled primary antibody being bound to the antigen of the antigen-antibody complex;

d. washing the sandwich complex to remove non bound debris; and
e. mixing the sandwich complex in a reactant solution to form an indicator indicating the presence of a specific cancer.

4. The method as claimed in claim 3 including repeating steps a and c at least one time.

5. The method as claimed in claim 3 including repeating steps a and c three times.

6. The method as claimed in claim 3 including repeating steps a and c a plurality of times.

7. The method as claimed in claim 3 including the step of mixing said urine with a buffering solution before causing urine flow through the antibody bead means.

8. A method of collecting antigen from urine for testing for cancer comprising the steps of:
   a. mixing a buffer solution in urine;
   b. withdrawing the buffered urine into a syringe means containing a filter and beads with immobilized antibodies to obtain a concentration of antigen on said beads with immobilized antibodies;
   c. washing the complexed antigen-antibody beads to remove the stray ligands and debris;
   d. mixing the antigen-antibody complex beads with a prelabelled primary antibody solution to form a sandwich complex with the prelabelled primary antibody fastening on to the captured antigen receptor sites;
   e. washing the sandwich antigen-antibody complex to remove stray ligands and debris; and
   f. treating the washed sandwich complex with a coloring reagent to obtain a colored solution indicating the presence of a specific antigen cancer marker.

9. The method as claimed in claim 8 including the step of adding another solution to said reactant solution.

10. The method as claimed in claim 9 wherein said another solution added to said reactant solution is hydrogen peroxide.

11. The method as claimed in claim 8 wherein said prelabelled primary antibody is labelled with HRP.

12. The method as claimed in claim 8 wherein said reactant solution is ABTS.

13. The method as claimed in claim 8 wherein said reactant solution is TMB.

14. The method as claimed in claim 8 wherein said reactant solution is OPD.

* * * * *